(12) United States Patent
Nakayama

(10) Patent No.: US 8,420,399 B2
(45) Date of Patent: Apr. 16, 2013

(54) ANALYTICAL METHOD OF HEMOGLOBIN

(75) Inventor: Yusuke Nakayama, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 13/210,835

(22) Filed: Aug. 16, 2011

(65) Prior Publication Data

US 2012/0040466 A1    Feb. 16, 2012

(30) Foreign Application Priority Data

Aug. 16, 2010   (JP) ................. 2010-181842

(51) Int. Cl.
*G01N 33/72*     (2006.01)
*G01N 27/447*   (2006.01)
*G01N 21/17*     (2006.01)

(52) U.S. Cl.
USPC ......... 436/66; 436/63; 436/119; 436/161; 436/164; 436/174; 436/177; 436/149; 436/150; 422/68.1; 422/70; 422/82.01; 204/450; 210/656; 210/198.2

(58) Field of Classification Search .......... 436/63, 436/66, 67, 119, 127, 149, 150, 161, 164, 436/166, 174, 176, 177, 178; 422/68.1, 70, 422/82.05, 82.09, 82.01; 204/450, 451, 452, 204/600; 210/656, 198.2
See application file for complete search history.

(56) References Cited

U.S. PATENT DOCUMENTS

| | | | | |
|---|---|---|---|---|
| 4,670,417 A | * | 6/1987 | Iwasaki et al. | 514/13.5 |
| 5,611,903 A | | 3/1997 | Janssens et al. | 204/454 |
| 5,814,487 A | * | 9/1998 | Knuth et al. | 435/74 |
| 5,952,464 A | * | 9/1999 | Mertens et al. | 530/329 |
| 2009/0200166 A1 | * | 8/2009 | Nakayama et al. | 204/451 |
| 2010/0006436 A1 | | 1/2010 | Oishi et al. | 204/451 |
| 2010/0116660 A1 | | 5/2010 | Tanaka et al. | 204/452 |
| 2010/0258440 A1 | * | 10/2010 | Sugiyama et al. | 204/451 |

FOREIGN PATENT DOCUMENTS

| | | |
|---|---|---|
| EP | 0142642 A1 | 5/1985 |
| EP | 2144055 A1 | 1/2010 |
| JP | 9-105739 | 4/1997 |
| JP | 2000258420 * | 9/2000 |
| JP | 2009-109230 | 5/2009 |
| JP | 2009-186445 | 8/2009 |
| WO | WO 2008/136465 | 11/2008 |

OTHER PUBLICATIONS

Overly et al. Abstract from the Journal of Laboratory and Clinical Medicine, vol. 69, No. 1, 1967, pp. 62-87.*

Lapolla et al., "Direct Evaluation of Glycated and Glyco-oxidized Globins by Matrix-assisted Laser Desorption/Ionization Mass Spectrometry," Rapid Communications in Mass Spectrometry, 13: 8-14 (1999).

Lewis et al., "An Accurate Method for the Determination of Carboxyhemoglobin in Postmortem Blood Using GC-TCD," Journal of Analytical Toxicology, 28: 59-62 (2004).

Extended European Search Report dated Oct. 31, 2011 issued in the corresponding European Application No. 11177541.7, dated Oct. 31, 2011.

* cited by examiner

*Primary Examiner* — Maureen Wallenhorst

(74) *Attorney, Agent, or Firm* — Morgan, Lewis & Bockius LLP

(57) ABSTRACT

A method for analyzing hemoglobin in a sample by separation analysis while suppressing the denaturation of the hemoglobin includes separating hemoglobin in the presence of at least one of a sulfurous acid compound and a dithionous acid compound.

6 Claims, 2 Drawing Sheets

ANALYTICAL METHOD OF HEMOGLOBIN

CROSS-REFERENCE TO RELATED APPLICATION

This application is based upon Japanese Application No. JP 2010-181842, filed Aug. 16, 2010, which is hereby incorporated by reference in its entirety.

BACKGROUND OF THE INVENTION

1. Field of the Invention

The present invention relates to an analytical method of hemoglobin and a kit for analysis.

2. Description of Related Art

Hemoglobin A1c is a glycated hemoglobin, and is used as an index of a level of blood glucose for checking lifestyle diseases including diabetes and metabolic syndrome and managing blood sugar. It is expected to become one of important indexes in the future. The amount of stable hemoglobin A1c is a particularly important index, and there is a desire for a technology capable of measuring the amount of stable hemoglobin A1c more precisely. Stable hemoglobin A1c can be analyzed by separation analysis techniques such as electrophoresis or HPLC.

Electrophoresis includes various methods depending upon the presence/absence of a support, the kind of support, etc., and examples of the electrophoresis include polyacrylamide electrophoresis, agarose gel electrophoresis, starch gel electrophoresis, paper electrophoresis, cellulose acetate membrane electrophoresis, electrochromatography, free flow electrophorese, and capillary electrophoresis. As an analytical method using agarose gel electrophoresis, for example, a method for separating glycated hemoglobin using agarose gel with sulfonated polysaccharides such as chondroitin sulfate added thereto is proposed. As an analytical method using capillary electrophoresis, for example, a method for analyzing a sample within a short period of time by using electrodynamic chromatography with an running buffer containing a polyanion and a polycation of chondroitin sulfate or the like, (JP 09 (1997)-105739 A), a method for forming a microchip of an electrophoresis apparatus to miniaturize an analytical apparatus (JP 2009-186445 A and JP 2009-109230 A), and the like are proposed.

SUMMARY OF THE INVENTION

In the case of analyzing hemoglobin by separation analysis such as electrophoresis or HPLC, there is a problem that the hemoglobin is denatured and an error is likely to be caused in a measured value. For example, in the case of electrophoresis, hemoglobin is oxidized (to met hemoglobin) along with an increase in temperature of a running buffer. Even in the case of HPLC, hemoglobin also may be oxidized (to met hemoglobin) with the passage of a time. The present invention provides an analytical method capable of suppressing the denaturation of hemoglobin in separation analysis.

The present invention relates to an analytical method for analyzing hemoglobin in a sample by separation analysis, which includes separating hemoglobin in the presence of at least one of a sulfurous acid compound and a dithionous acid compound.

In another aspect, the present invention relates to a kit for analysis using the above-mentioned analytical method, including a composition containing a sulfurous acid compound or a dithionous acid compound, used as a sample preparation buffer, a running buffer, or a mobile phase, and an instruction manual describing the analytical method.

According to the present invention, for example, hemoglobin can be subjected to separation analysis while the denaturation of the hemoglobin is suppressed. Preferably, according to the present invention, hemoglobin can be analyzed precisely by suppressing the denaturation of the hemoglobin.

DETAILED DESCRIPTION OF THE INVENTION

Figure 1A:
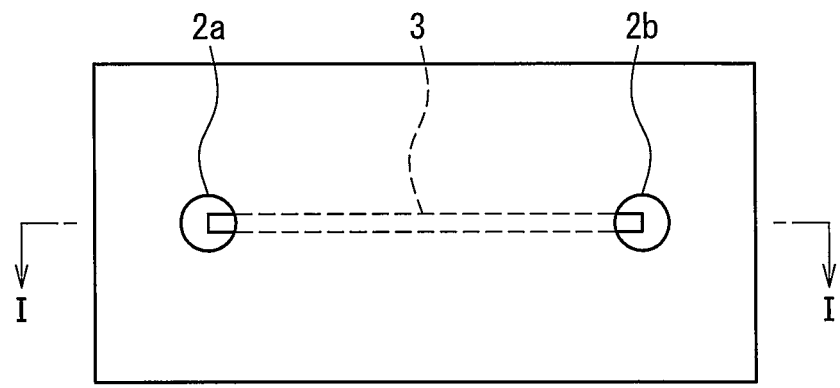
FIG. 1A is a conceptual view illustrating an exemplary configuration of an electrophoresis chip that can be used in a method of the present invention.

The present invention is based on the finding that, in separation analysis of hemoglobin, hemoglobin is oxidized (to met hemoglobin) with the passage of time and/or as the analysis condition becomes acid, and the absorption characteristics of hemoglobin change (maximum wavelength: 415 nm→405 nm), which may cause an error in a measured value. The present invention is also based on the finding that the denaturation of hemoglobin in separation analysis can be suppressed by the use of at least one of a sulfurous acid compound and a dithionous acid compound. That is, the present invention relates to an analytical method (hereinafter, also referred to as "analytical method of the present invention") for analyzing hemoglobin in a sample by separation analysis, including separating hemoglobin in the presence of at least one of a sulfurous acid compound and a dithionous acid compound. The present invention exhibits, for example, that separation analysis of hemoglobin can be performed while the denaturation of the hemoglobin is suppressed. The present invention preferably exhibits that hemoglobin can be analyzed precisely by suppressing the denaturation of the hemoglobin.

Although the details of a mechanism in which the denaturation of hemoglobin is suppressed in the presence of at least one of a sulfurous acid compound and a dithionous acid compound is not clear, it is conjectured that the sulfurous acid compound and the dithionous acid compound are oxidized in place of hemoglobin with respect to the oxidation caused in the course of analysis and function as a sacrificial reagent that prevents the oxidation of hemoglobin. It should be noted that the present invention need not be limited to the above-mentioned mechanism.

[Separation Analysis]

The term "separation analysis" as used herein refers to an analytical method using electrophoresis, chromatography, etc., including separating, detecting, and measuring a substance to be analyzed. The term "electrophoresis" as used herein refers to a method for separating a substance, using the difference in a mobility in an electric field caused by the difference in a size, charge, etc. The analytical method of the present invention can be used for analysis using various electrophoresis techniques such as polyacrylamide electrophoresis, agarose gel electrophoresis, starch gel electrophoresis, paper electrophoresis, cellulose acetate membrane electrophoresis, electrochromatography, free flow electrophorese, and capillary electrophoresis. Of those, the analytical method of the present invention is suitable for capillary electrophoresis, preferably electrochromatography, and particularly capillary electrophoresis using an electrophoresis microchip.

[Hemoglobin]

The term "hemoglobin" as used herein includes hemoglobin in a plurality of forms in blood, and examples thereof include normal hemoglobin, glycated hemoglobin, mutant hemoglobin, and modified hemoglobin. More specific examples thereof include hemoglobin AO (HbAO), hemoglobin A1c (HbA1c), hemoglobin A2 (HbA2), hemoglobin S (HbS, sickle cell hemoglobin), hemoglobin (HbF, fetal hemoglobin), hemoglobin M (HbM), hemoglobin C (HbC), methohemoglobin, carbamylated hemoglobin, and acetylated hemoglobin. Examples of the HbA1c include stable HbA1c and unstable HbA1c. The term "analysis of hemoglobin" as used herein includes separating hemoglobin into stable HbA1c, and unstable HbA1c and HbAO, and detecting and/or measuring the stable HbA1c and/or unstable HbA1c.

Hemoglobin is classified depending upon the state of oxidation and the presence/absence of a bond to oxygen. Hemoglobin bonded to oxygen is called oxyhemoglobin or oxygenated hemoglobin. Further, hemoglobin that is not bonded to oxygen is called deoxyhemoglobin or reduced hemoglobin. Further, hemoglobin in which iron (Fe) atoms in a heme portion become trivalent and oxygen bonding strength is lost is called met hemoglobin or oxidized hemoglobin. The term "denatured hemoglobin" as used herein includes met hemoglobin.

[Sulfurous Acid Compound and Dithionous Acid Compound]

The term "sulfurous acid compound" as used herein includes sulfurous acid, sulfite, hydrogen sulfite, and disulfite, and the form of a salt thereof includes, but is not limited to, a sodium salt, an ammonium salt, and a potassium salt. Specific examples of the sulfurous acid compound include sodium sulfite ($Na_2SO_3$), sodium hydrogen sulfite ($NaHSO_3$), and disodium disulfite (sodium pyrosulfite, $Na_2S_2O_5$). The term "dithionous acid compound" as used herein includes dithionous acid and dithionite, and the form of a salt includes, but is not limited to, a sodium salt, an ammonium salt, and a potassium salt. A specific example of the dithionous acid compound is sodium dithionite ($Na_2S_2O_4$).

[Sample, Running Buffer, Mobile Phase]

The "sample" as used herein refers to a sample prepared from a sample material. As an example of the sample material, there is a biological sample, preferably a sample containing hemoglobin. Examples of the biological sample include, but are not limited to, blood, a substance derived from blood containing a red blood cell component, saliva, and cerebrospinal fluid. As an example of the blood, there is blood collected from a living body, preferably blood of an animal, more preferably blood of mammals, still more preferably blood of a human. As an example of the substance derived from blood containing a red blood cell component, there is a substance containing a red blood cell component, which is separated or prepared from blood, and examples thereof include, but are not limited to, a blood cell fraction with blood plasma removed therefrom, a blood cell concentrate, a frozen dry substance of blood or a blood cell, a hemolytic sample obtained by hemolyzing whole blood, centrifuged blood, and naturally precipitated blood. The "sample preparation buffer (sample diluent)" as used herein is used for being mixed with a sample material to prepare a sample, and includes, for example, a liquid for diluting a sample material. The concentration (content) of a sample material in a sample is preferably 1 to 30% by weight from the viewpoint of suppressing the denaturation of hemoglobin.

The term "running buffer" as used herein refers to a liquid that fills or permeates a channel, a carrier, a space for separating a sample in electrophoresis, etc. The term "mobile phase" as used herein refers to a mobile phase used in liquid chromatography.

[Buffer]

It is preferred that a sample, a running buffer, and a mobile phase used in the present invention contain a buffer from the viewpoint of the stabilization of the sample and the suppression of change in pH. The sample, the running buffer, and the mobile phase may contain one kind or a plurality of kinds of buffers. As the buffer, a known solution having a buffer function can be used, and examples thereof include, but are not limited to, organic acids such as citric acid, succinic acid, tartaric acid, and malic acid, and salts thereof; amino acids such as glycin, taurine, and arginine; and inorganic acids such as hydrochloric acid, nitric acid, sulfuric acid, phosphoric acid, boric acid, and acetic acid, and salts thereof.

[Analytical Method of Hemoglobin]

As described above, the analytical method of the present invention relates to a method for analyzing hemoglobin in a sample by separation analysis, including separating hemoglobin in the presence of at least one of a sulfurous acid compound and a dithionous acid compound. One embodiment of "separating hemoglobin in the presence of at least one of a sulfurous acid compound and a dithionous acid compound" is separating hemoglobin in electrophoresis or liquid chromatography, using a running buffer or a mobile phase containing at least one of a sulfurous acid compound and a dithionous acid compound.

For example, in electrophoresis using an electrophoresis microchip or the like, the ambient temperature of hemoglobin reaches 30° C. or higher or 40° C. or more, in some cases, 50° C. or higher in the process of separating hemoglobin, under which condition hemoglobin is highly likely to be oxidized (to met hemoglobin). Further, even at room temperature or low temperature, there is a possibility that hemoglobin may be oxidized (to met hemoglobin) in the presence of dissolved oxygen or an oxidized substance. The analytical method of the present invention is capable of suppressing such denaturation of hemoglobin.

[pH]

The pH of a running buffer and a mobile phase in separation of hemoglobin is preferably 6 or less, such as about 5.5 or less, such as about 5 or less from the viewpoint of the stability of a sulfurous acid compound and a dithionous acid compound. Further, the pH is preferably 3 or more, such as about 3.5 or more, such as about 4 or more from the viewpoint of suppressing the denaturation of hemoglobin. From the similar viewpoint, the pH of a sample and a sample preparation buffer is preferably in the similar range.

[Concentration]

The concentration of a sulfurous acid compound and a dithionous acid compound in the separation of hemoglobin is preferably 0.001 mM or more, such as about 0.01 mM or more, such as about 0.1 mM or more from the viewpoint of suppressing the denaturation of hemoglobin. Above all, from the viewpoint of preventing hemoglobin from being oxidized to met hemoglobin, the concentration of sodium hydrogen sulfite, sodium sulfite, and sodium disulfite is preferably 0.5 mM or more, such as about 1 mM or more; and the concentration of sodium dithionite is 0.25 mM or more, such as about 0.5 mM or more.

Further, from the viewpoint of measuring hemoglobin while keeping the state of oxy Hb without deoxylating (reducing) hemoglobin, the concentration of a sulfurous acid compound or a dithionous acid compound is preferably 20 mM or less, such as about 10 mM or less. Specifically, in the case of using a sulfurous acid compound (sodium hydrogen sulfite, sodium sulfite), from the viewpoint of measuring hemoglobin while keeping the state of oxy Hb without deoxylating (reducing) hemoglobin, the concentration is preferably 20 mM or less, such as about 15 mM or less, such as about 10 mM or less. In the case of using sodium disulfite, the concentration is preferably 10 mM or less, such as about 5 mM or less, such as about 2 mM or less from the similar viewpoint. Further, in the case of using a dithionous acid compound (sodium dithionite), the concentration is preferably about 10 mM or less, such as about 5 mM or less, such as about 2 mM or less from the similar viewpoint.

It is preferred that the concentration of a sulfurous acid compound or a dithionous acid compound in a running buffer and a mobile phase is also set to be in the above-mentioned range. Thus, it is preferred to use a sample preparation buffer (sample diluent) allowing the concentration of a sulfurous acid compound or a dithionous acid compound to be set in the above-mentioned range even in the case of preparing a sample.

In the analytical method of the present invention, hemoglobin is measured preferably in either a deoxy Hb or oxy Hb state, more preferably in the oxy Hb state, from the viewpoint of suppressing a measurement error.

[Spectrophotometer]

In the analytical method of the present invention, it is preferred to detect and measure hemoglobin by measuring an absorbance with a spectrophotometer from the viewpoint of the ease of detection of hemoglobin. In this case, it is preferred that the wavelength of light radiated from a light source of the spectrophotometer is about 300 nm or more from the viewpoint of suppressing the decomposition of a sulfurous acid compound and a dithionous acid compound.

[Kit for Analysis]

Another aspect of the present invention relates to a kit for analysis using the analytical method according to claim 1, comprising a composition containing a sulfurous acid compound or a dithionous acid compound, used as a sample preparation buffer, a running buffer, or a mobile phase, and an instruction manual describing the analytical method. The kit for analysis of the present invention may include the case where the instruction manual is provided on the Web without being packaged in the kit for analysis of the present invention.

In the kit for analysis of the present invention, a sample preparation buffer, a running buffer, or a mobile phase is as described above. Further, as one embodiment, the kit for analysis of the present invention preferably further includes an electrophoresis chip. It is preferred that the electrophoresis chip includes a sample storage tank, a running buffer storage tank, and a passage, and the sample storage tank is communicated with the running buffer storage tank through the passage. Further, the passage of the electrophoresis chip may be filled with the above-mentioned running buffer. As an example of the electrophoresis chip, there is an electrophoresis chip described in International Publication No. WO2008/136465.

Hereinafter, the present invention will be described further by way of examples and comparative examples. It should be noted that the present invention should not be interpreted as being limited to the following examples.

EXAMPLE

[Hb Denaturation Suppressing Effect]

A sample was prepared from a sample material (whole blood) as described below, and the presence/absence of Hb denaturation was determined by the following Hb denaturation detection method.

<Method for Preparing a Sample>

To 1.5 mL of a 100 mM malic acid-arginine buffer solution (pH 5.0), an additive was added so as to obtain a final concentration in the following Table 1 to prepare a sample preparation buffer. Then, 0.01 mL of whole blood as a sample material was added and mixed to 1.49 mL of the sample preparation buffer to prepare a sample (Examples 1 to 8, Comparative Examples 1 to 7). As the additive, sodium hydrogen sulfite ($NaHSO_3$, Nacalai Tesque Inc.) was used in Examples 1 and 5; sodium sulfite ($Na_2SO_3$, Nacalai Tesque Inc.) was used in Examples 2 and 6; disodium disulfite (sodium pyrosulfite, $Na_2S_2O_5$, Nacalai Tesque Inc.) was used in Examples 3, 7, and 8; sodium dithionite ($Na_2S_2O_4$, Nacalai Tesque Inc.) was used in Example 4; benzyltrimethylammonium (Wako Pure Chemical Industries, Ltd.) was used in Comparative Example 2; reduced glutathione (Nacalai Tesque Inc.) was used in Comparative Example 3; TAPS—sulphonate ($C_7H_{18}BrNo_2S_2$, Wako Pure Chemical Industries, Ltd.) was used in Comparative Example 4; ascorbic acid (Wako Pure Chemical Industries, Ltd.) was used in Comparative Example 5; and hydroxylamine sulfate (Nacalai Tesque Inc.) was used in Comparative Example 6; and nitrous acid (Wako Pure Chemical Industries, Ltd.) was used in Comparative Example 7. No additive was added in Comparative Example 1.

<Detection of Hb Denaturation>

The samples in Examples 1 to 8 and Comparative Examples 1 to 7 prepared as described above were incubated at 50° C. for 60 seconds, and an absorbance at 400 nm was measured before and after the incubation, whereby a change amount (absorbance after 60 seconds–initial absorbance) was obtained. Table 1 shows the results. An absorbance was measured with a spectrophotometer (trade name: UV-2400PC, Shimazu Corporation).

TABLE 1

| | Additive | Concentration | Absorbance at 400 nm (abs) | | Change amount (60 s − 0 s) | State of Hb |
| --- | --- | --- | --- | --- | --- | --- |
| | | | Initial value | After 60 seconds | | |
| Example 1 | Sodium hydrogen sulfite $NaHSO_3$ | 5 mM | 0.57 | 0.57 | 0.00 | Remain unchanged (oxy Hb) |
| Example 2 | Sodium sulfite $Na_2SO_3$ | 5 mM | 0.54 | 0.54 | 0.00 | Remain unchanged (oxy Hb) |
| Example 3 | Disodium disulfite $Na_2S_2O_5$ (sodium pyrosulfite) | 2 mM | 0.52 | 0.52 | 0.00 | Remain unchanged (oxy Hb) |

TABLE 1-continued

|  | Additive | Concentration | Absorbance at 400 nm (abs) Initial value | Absorbance at 400 nm (abs) After 60 seconds | Change amount (60 s − 0 s) | State of Hb |
|---|---|---|---|---|---|---|
| Example 4 | Sodium dithionite $Na_2S_2O_4$ | 2 mM | 0.56 | 0.56 | 0.00 | Remain unchanged (oxy Hb) |
| Example 5 | Sodium hydrogen sulfite $NaHSO_3$ | 20 mM | 0.58 | 0.51 | −0.07 | Deoxylated |
| Example 6 | Sodium sulfite $Na_2SO_3$ | 20 mM | 0.51 | 0.46 | −0.05 | Deoxylated |
| Example 7 | Disodium disulfite $Na_2S_2O_5$ (sodium pyrosulfite) | 20 mM | 0.57 | 0.47 | −0.10 | Deoxylated |
| Example 8 | Disodium disulfite $Na_2S_2O_5$ (sodium pyrosulfite) | 5 mM | 0.54 | 0.53 | −0.01 | Deoxylated |
| Comparative Example 1 | — (None) | — | 0.53 | 0.63 | 0.10 | Oxidized to met hemoglobin/precipitated |
| Comparative Example 2 | Benzyltrimethyl ammonium | 20 mM | 0.47 | 0.53 | 0.06 | Oxidized to met hemoglobin/precipitated |
| Comparative Example 3 | Reduced glutathione | 20 mM | 0.46 | 0.56 | 0.10 | Oxidized to met hemoglobin/precipitated |
| Comparative Example 4 | TAPS-sulphonate | 20 mM | 0.57 | 0.82 | 0.25 | Oxidized to met hemoglobin/precipitated |
| Comparative Example 5 | Ascorbic acid | 20 mM | 0.53 | 0.83 | 0.30 | Oxidized to met hemoglobin/precipitated |
| Comparative Example 6 | Hydroxyamine sulfate | 20 mM | 0.50 | 0.84 | 0.34 | Oxidized to met hemoglobin/precipitated |
| Comparative Example 7 | Nitrous acid | 20 mM | 0.42 | 0.50 | 0.08 | Oxidized to met hemoglobin/precipitated |

As shown in Table 1, in the samples of Examples 1 to 4, the absorbance did not change even after incubation at 50° C. for 60 seconds, and the state of oxyhemoglobin was kept with the denaturation of hemoglobin suppressed. On the other hand, in Examples 5 to 8, the absorbance at 50° C. after 60 seconds decreased, and hemoglobin became deoxyhemoglobin (reduced hemoglobin). Although the state of deoxyhemoglobin is different from the original state of hemoglobin in blood, deoxyhemoglobin is stable, and hence, hemoglobin can be analyzed even in this state. On the other hand, in Comparative Examples 1 to 7, the absorbance at 50° C. after 60 seconds increased, hemoglobin was denatured, that is, oxidized to met hemoglobin, and precipitation of the met hemoglobin was partially observed.

[Analysis of Hemoglobin]

The samples of Examples 1 to 8 were electrophoresed, using the following microchip and conditions, and HbAO, unstable HbA1c, and stable HbA1c in the sample were detected.

<Microchip>

Figure 1B:
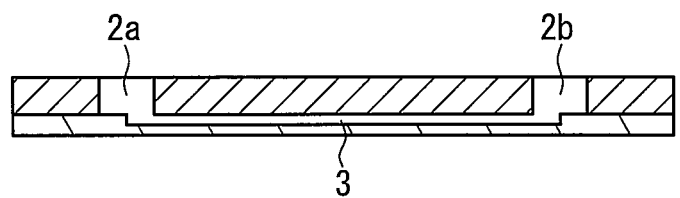
FIG. 1B is a cross-sectional view taken along a line I-I of the electrophoresis chip illustrated in FIG. 1A.

An electrophoresis chip (made of polymethacrylate, length: 70 mm, width: 30 mm) having a structure illustrated in FIG. 1 was used. The electrophoresis chip had a rectangular passage 3, and a sample storage tank 2a (capacity: 0.05 mL) and a running buffer storage tank 2b (capacity: 0.05 mL) were formed at both ends of the passage 3. The length of the passage 3 was set to be 40 mm, and the width and depth of the passage 3 were respectively set to be 40 μm (inner diameter of the passage: 40 μm). Further, the distance between the center of the sample storage tank 2a and the center of the running buffer storage tank 2b was set to be 46 mm.

[Running Buffer]

A running buffer containing 1.0% by weight of chondroitin sulfuric acid C sodium salt (Seikagaku Corporation), 1 mM $NaN_3$, 100 mM malic acid-arginine buffer solution (pH 5.0), 2 mM sodium propionate, and 2 mM CyDTA, and further containing the same sulfurous acid compound or dithionous acid compound as that of each sample of Examples 1 to 8 in the same concentration as that of each sample of Examples 1 to 8 was used. The running buffer was adjusted to pH 5.0 with L-arginine.

[Electrophoresis]

A running buffer was introduced into the running buffer storage tank 2b of the electrophoresis chip, and the passage 3 was filled with the running buffer by a capillary action. Then, a sample was introduced into the sample storage tank 2a. Electrodes were inserted into the sample storage tank 2a and the running buffer storage tank 2b, respectively, and a voltage of 1,400 V was applied to the inserted electrodes to perform electrophoresis. An absorbance at 400 nm was measured at a position of 20 mm from the end of the passage 3 on the sample storage tank 2a side.

Figure 2:
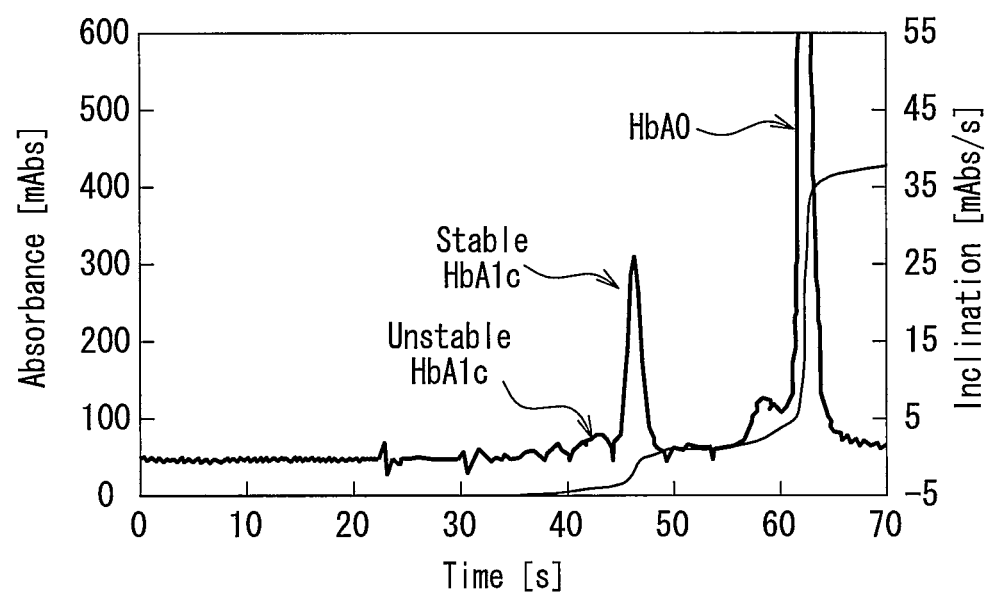
FIG. 2 is a graph illustrating exemplary results of Example 1.

FIG. 2 illustrates an example (results corresponding to Example 1) of the obtained electroferrogram. Further, the analysis results using the samples of Examples 2 to 8 were similar to those in FIG. 2.

FIG. 2 illustrates the actually obtained electroferrogram, and a change in the absorbance obtained by processing the electroferrogram. The X-axis represents an electrophoresis time (seconds). The Y-axis (left side) represents an actually measured absorbance (mAbs). The Y-axis (right side) represents an absorbance per unit time obtained by processing the actually measured absorbance (mAbs/sec). Further, in FIG. 2, unstable A1c, stable A1c, and HbAO represent peaks of unstable HbA1c, stable HbA1c, and HbAO. As illustrated in FIG. 2, HbA1c and HbAO were separated clearly from the sample of Example 1, and further, HbA1c was separated clearly into unstable HbA1c and stable HbA1c. More specifically, it was shown that the presence of a sulfurous acid compound or a dithionous acid compound in a sample or a running buffer does not have an adverse effect on the detection method using a microchip.

[Dissolved Oxygen Removing Effect]

To 10 mL of a 100 mM malic acid-arginine buffer solution (pH 5.0), an additive was added so as to obtain a final concentration in the following Table 2 to prepare solutions (Reference Examples 1 to 5), and dissolved oxygen at 30° C. and 50° C. was measured under the following conditions. As the additive, sodium hydrogen sulfite (NaHSO$_3$, Nacalai Tesque Inc.) was used in Reference Example 1; sodium sulfite (Na$_2$SO$_3$, Nacalai Tesque Inc.) was used in Reference Example 2; disodium disulfite (sodium pyrosulfite Na$_2$S$_2$O$_4$, Nacalai Tesque Inc.) was used in Reference Example 3; and sodium dithionite (Na$_2$S$_2$O$_4$, Nacalai Tesque Inc.) was used in Reference Example 4. No additive was added in Reference Example 5.

[Method for Measuring Dissolved Oxygen]

Dissolved oxygen was measured using a blood gas analysis apparatus (trade name: ABL5, Tadiometer Co., Ltd.). Table 2 shows the results.

TABLE 2

| Additive | | Concentration | Amount of dissolved oxygen (mg/L) | | Discharge amount |
| --- | --- | --- | --- | --- | --- |
| | | | 30° C. | 50° C. | 30° C.-50° C. |
| Reference Example 1 | Sodium hydrogen sulfite NaHSO$_3$ | 5 mM | 4.06 | 3.20 | 0.86 |
| Reference Example 2 | Sodium sulfite Na$_2$SO$_3$ | 5 mM | 4.13 | 3.14 | 0.99 |
| Reference Example 3 | Disodium disulfite Na$_2$S$_2$O$_5$ (sodium pyrodithionite) | 5 mM | 3.77 | 2.94 | 0.83 |
| Reference Example 4 | Sodium dithionite Na$_2$S$_2$O$_4$ | 5 mM | 0.00 | 0.00 | 0.00 |
| Reference Example 5 | - (None) | — | 4.20 | 3.49 | 0.71 |

As shown in Table 2, in the case of the sulfurous acid compound, a dissolved oxygen removing effect was exhibited in a heated state. Further, it is understood that, since the reaction does not proceed without being heated, a running buffer and the like containing a sulfurous acid compound can be stored. On the other hand, the dithionous acid compound reacts rapidly to remove dissolved oxygen immediately. However, the reactivity of the dithionous acid compound is high, and hence, it is understood that the sulfurous acid compound is preferred when applied to a solution to be stored.

[Relationship Between the Concentration of a Sulfurous Acid Compound and a Dithionous Acid Compound, and the Change in Absorbance]

The change in absorbance after incubation at 50° C. for 60 seconds was measured under conditions similar to those for the measurement of a change in absorption in Table 1, except for changing the addition concentration of a sulfurous acid compound and a dithionous acid compound to those in Table 3. Table 3 and FIG. 3 show the results.

TABLE 3

| | Change in absorbance (400 nm/60 sec) | | | |
| --- | --- | --- | --- | --- |
| Addition concentration | Sodium hydrogen sulfite | Sodium sulfite | Disodium disulfite | Sodium dithionite |
| 0 mM | 0.10 | 0.10 | 0.10 | 0.10 |
| 0.5 mM | 0.04 | 0.06 | 0.03 | 0.00 |
| 1 mM | 0.00 | 0.00 | 0.00 | 0.00 |
| 2 mM | 0.00 | 0.00 | 0.00 | 0.00 |
| 5 mM | 0.00 | 0.00 | −0.01 | −0.05 |
| 10 mM | 0.00 | 0.00 | −0.05 | −0.09 |
| 15 mM | −0.05 | −0.02 | −0.08 | −0.11 |
| 20 mM | −0.07 | −0.05 | −0.10 | −0.13 |

Figure 3:
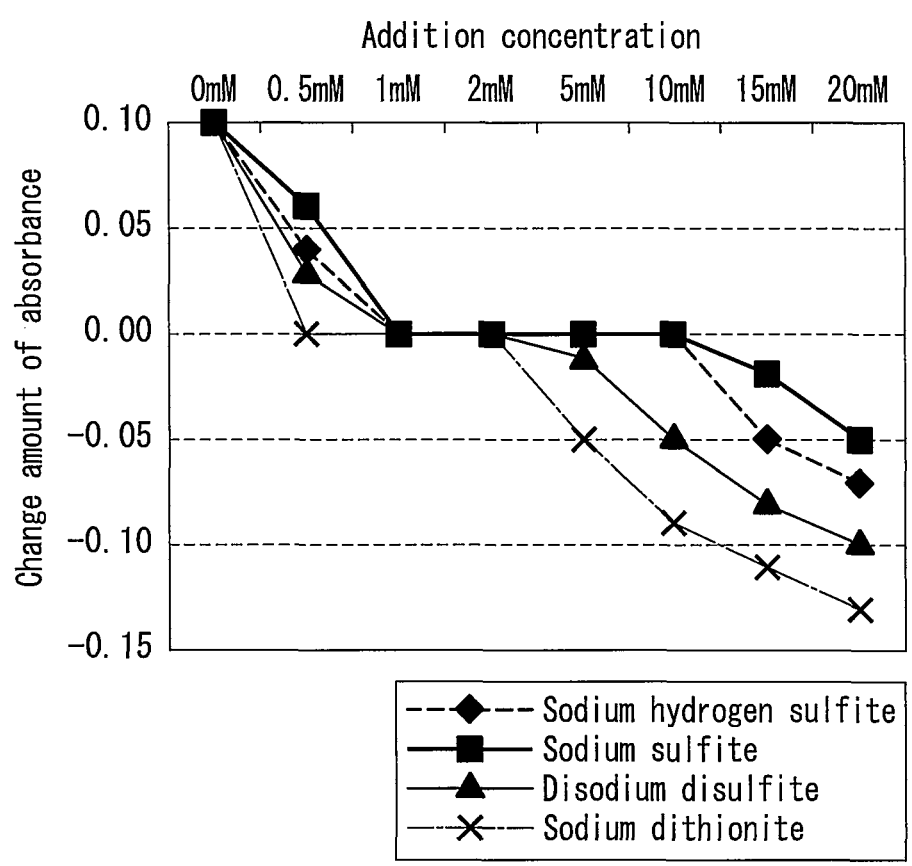
FIG. 3 is a graph showing an exemplary relationship between the concentrations of a sulfurous acid compound and a dithionous acid compound and the change in absorbance of light.

As shown in Table 3 and FIG. 3, the sulfurous acid compound and the dithionous acid compound respectively set the change in absorbance to be zero, that is, they suppressed the denaturation of hemoglobin. The concentration of sodium hydrogen sulfite and sodium sulfite, at which the change in absorbance was zero, was 1 to 10 mM; that of sodium disulfite was 1 to 2 mM; and that of sodium dithionite was 0.5 to 2 mM.

The analytical method of the present invention is useful in various fields such as medical care, clinical examination, and the treatment/prevention of diabetes.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. An analytical method for analyzing hemoglobin in a sample, comprising:
   separating hemoglobin in a sample by electrophoresis or liquid chromatography, using a running buffer or a mobile phase containing
   at least one of a sulfurous acid compound and
   a dithionous acid compound,
wherein said sample is prepared from blood collected from a living body.

2. The analytical method according to claim 1, wherein pH of the sample, the running buffer, or the mobile phase is about 3 to about 6.

3. The analytical method according to claim 2, wherein a concentration of the sulfurous acid compound or the dithionous acid compound in the running buffer, or the mobile phase is about 10 mM or less.

4. The analytical method according to claim 1, further comprising detecting or measuring the hemoglobin with a spectrophotometer.

5. The analytical method according to claim 4, wherein a wavelength of light radiating from a light source of the spectrophotometer is about 300 nm or more.

6. The analytical method according to claim 1, wherein an ambient temperature of the hemoglobin during the separating is 30° C. or higher.

* * * * *